United States Patent [19]
Vigil et al.

[11] Patent Number: 5,681,281
[45] Date of Patent: Oct. 28, 1997

[54] CATHETER WITH FLUID MEDICATION INJECTORS

[75] Inventors: Dennis M. Vigil, San Diego, Calif.; Peter Barath, Hinsdale, Ill.

[73] Assignee: InterVentional Technologies, Inc., San Diego, Calif.

[21] Appl. No.: 541,526

[22] Filed: Oct. 10, 1995

Related U.S. Application Data

[63] Continuation-in-part of Ser. No. 500,121, Jul. 10, 1995.

[51] Int. Cl.$^6$ .................................................. A61M 29/00
[52] U.S. Cl. .................................................. 604/96
[58] Field of Search .................... 604/96–104, 164, 604/264, 48, 49, 51–53; 606/1, 191–200; 128/898

[56] References Cited

U.S. PATENT DOCUMENTS

| | | |
|---|---|---|
| 3,635,223 | 1/1972 | Klieman . |
| 4,140,126 | 2/1979 | Choudhury . |
| 4,273,128 | 6/1981 | Lary . |
| 4,441,509 | 4/1984 | Kotsifas et al. . |
| 4,465,072 | 8/1984 | Taheri . |
| 5,009,659 | 4/1991 | Hamlin et al. . |
| 5,100,425 | 3/1992 | Fischell et al. . |
| 5,112,305 | 5/1992 | Barath .................... 604/96 |
| 5,156,610 | 10/1992 | Reger . |
| 5,196,024 | 3/1993 | Barath . |
| 5,320,634 | 6/1994 | Vigil et al. . |
| 5,336,178 | 8/1994 | Kaplan et al. .................... 604/53 |
| 5,354,279 | 10/1994 | Hofling .................... 604/164 |

FOREIGN PATENT DOCUMENTS

| | | |
|---|---|---|
| 0 567 788A1 | 3/1993 | European Pat. Off. . |
| 3519626 | 4/1986 | Germany . |
| 1547328 | 6/1979 | United Kingdom . |
| WO 94/23787 | 10/1994 | WIPO . |

*Primary Examiner*—Glenn Dawson
*Attorney, Agent, or Firm*—Nydegger & Associates

[57] ABSTRACT

A device for injecting medication into a vessel wall includes an inflatable balloon mounted on a catheter. Additionally, a plurality of tubular fluid passageways are longitudinally mounted on the balloon, and a plurality of injectors are mounted on each tubular passageway and in fluid communication therewith. During use of the device, the balloon is first positioned in a vessel. The balloon is then inflated to embed the injectors into the vessel wall. Next, a fluid medicament is introduced through each of the fluid passageways for further infusion through the passageways and through the injectors into the vessel wall.

17 Claims, 3 Drawing Sheets

CATHETER WITH FLUID MEDICATION INJECTORS

This is a continuation-in-part patent application of co-pending U.S. patent application Ser. No. 08/500,121, filed on Jul. 10, 1995, and entitled "CATHETER FOR INJECTING FLUID MEDICATION INTO AN ARTERIAL WALL."

FIELD OF THE INVENTION

The present invention pertains generally to invasive medical devices which are useful for the purpose of infusing fluid medicaments into a patient. More specifically, the present invention pertains to medical devices which can be inserted into a vessel of a patient's cardiovascular system. The present invention is particularly, but not exclusively, useful for infusing fluid medicaments directly into a vessel wall.

BACKGROUND OF THE INVENTION

Depending on the particular ailment it is known in the medical field that fluid medications can be infused directly into the wall of a vessel of a patient's cardiovascular system with beneficial results. For example, one such application involves the administration of medicaments into an arterial wall which will inhibit or prevent the restenosis of plaque in the artery. Any procedure involving the direct infusion of fluid medicaments into a vessel wall, however, requires the consideration of several factors. First, the procedure must be safe. For instance, due to the toxic nature of some medicaments, such a procedure must insure that only minimal amounts of medication are ever washed away into the blood stream and not actually infused into the vessel wall. Second, the device which infuses the medication into the vessel wall must be easy to use, accurate in its delivery capability and reliable in its operation.

Several devices have been suggested for the purpose of infusing fluid medicaments directly into a vessel wall. One example of such a device is disclosed in U.S. Pat. No. 5,354,279 which issued to Hofling for an invention entitled "Plural Needle Injection Catheter". The specific device disclosed in this patent employs prebent hollow needles which are extendable from a catheter to penetrate into a vessel wall. The extended needles are then used for infusion of the fluid medicament. U.S. Pat. No. 5,354,279 also discloses that an inner hose, which is so elastic that it can be expanded balloon-like, can be utilized to move the needles outwardly so as to engage or even pierce the surrounding vessel walls. Also, U.S. Pat. No. 5,364,356, was issued to Hofling for another invention entitled "Sleeve Catheter". This second patent to Hofling discloses a device which employs a balloon expandable sleeve that delivers fluid medication to a vessel wall. More specifically, this device of Hofling's includes a reconfigurable sleeve which is expanded by an inflatable balloon. It is intended that, as the sleeve expands, openings which are formed into the sleeve spread to discharge fluid medications onto the surface of the vessel walls. Still another example of a device for medicating a vessel wall is disclosed in U.S. Pat. No. 5,112,305 which issued to Barath et al. for an invention entitled "Catheter Device for Intramural Delivery of Therapeutic Agents". This same device is also disclosed in a related U.S. Pat. No. 5,242,397 which issued to Barath et al. for an invention entitled "Catheter Device and Method of Use for Intramural Delivery of Protein Kinase C and Tyrosine Protein Kinase Inhibitors to Prevent Restenosis after Balloon Angioplasty". Specifically, the device disclosed by Barath et al. employs a balloon which requires an initial slow filling of the balloon with a medicament to expand the balloon and position the balloon's surface against the vessel wall. This initial slow filling is then followed by a rapid filling of the balloon which reconfigures tubular extensions on the surface of the balloon for the infusion of medicaments through the tubular extensions and into the vessel wall.

None of the above discussed devices, however, address the problem from the same perspective as the present invention. Specifically, the present invention recognizes that it is preferable to have a mechanism for infusing medication into a vessel wall which is independent and separately operable from the mechanisms which position the device in the artery and which cause at least one medication injector to penetrate into the vessel wall. Consequently, as recognized by the present invention, it is preferable to isolate the mechanism for actual infusion of medications into the vessel wall from other operable mechanisms of the device. Further, the present invention recognizes that, depending on the nature and condition of the vessel wall, it is preferable to have the capability of selectively applying a variable force to the injectors of the device as they penetrate into the vessel wall.

In light of the above, it is an object of the present invention to provide a device for injecting medication into the wall of a vessel which includes a mechanism for penetrating a vessel wall with medication delivery injectors that is separate from the mechanism which infuses the medication into the vessel wall. It is another object of the present invention to provide a device for injecting medication into the wall of a vessel which can selectively vary the force that is used to penetrate the vessel wall with a fluid medication injector. Still another object of the present invention is to provide a device for injecting medication into the wall of a vessel which is easy to use, relatively simple to manufacture and comparatively cost effective.

SUMMARY OF THE INVENTION

In accordance with the present invention, a device for injecting medication into the wall of a vessel includes an inflatable PET balloon which is mounted on a multi-lumen catheter. A flexible tubular sleeve, preferably made of polyurethane, is provided. This sleeve effectively surrounds most of the inflatable balloon, and thereby creates an infusion chamber between the balloon and the sleeve. To create this chamber, the distal end of the tubular sleeve is attached directly onto the surface of the balloon, and the proximal end of the sleeve is extended proximally from the balloon. The open proximal end of the tubular sleeve thus establishes a port for fluid access into the infusion chamber.

For the device of the present invention, a plurality of injectors are mounted directly onto the sleeve and are placed in fluid communication with the infusion chamber. More specifically, each injector includes a base plate and a hollow protrusion which projects from the base of the injector to create a fluid channel through the injector. To establish a fluid path from the infusion chamber through the channel of the injector, the base of the injector is mounted onto the tubular sleeve over holes that may either be preformed into the sleeve or formed into the sleeve after the injectors have been attached to the sleeve.

The device of the present invention also includes a system for selectively inflating the balloon. As intended for the present invention, the balloon inflating system can be directly connected to a lumen of the catheter. The catheter lumen, in turn, is in fluid communication with the interior of the inflatable balloon. Additionally, the device includes a fluid pump which is engageable in fluid communication with the infusion chamber between the balloon and the sleeve for injecting fluid medicaments from a fluid source into the infusion chamber. Further, in an alternate embodiment of the present invention, instead of having single port injectors, a plurality of hollow protrusions can be formed onto the same base plate to create an injector having a plurality of outlet ports.

In the operation of the device of the present invention, a guidewire is first positioned into an artery of the patient. This is done to establish a mechanical pathway through the artery to the site where the fluid medication is to be infused. The extracorporeal end of the guidewire is then inserted into a lumen of the catheter and the balloon on the catheter is advanced over the guidewire and to the site where the medication is to be infused.

Once the balloon has been properly positioned for the infusion of fluid medicaments into the arterial wall, the balloon is inflated. This inflation of the balloon, in turn, urges the tubular sleeve to move outwardly with the expansion of the balloon. This action also causes the injectors to penetrate into the arterial wall. After the balloon has been inflated, and while the injectors remain penetrated into the arterial wall, the fluid pump is activated to inject fluid from the fluid source into the infusion chamber. Importantly, this pumping action also forces fluid from the infusion chamber through the injectors and into the arterial wall.

In yet another alternative embodiment of the present invention, the tubular sleeve which surrounds the inflatable balloon is replaced with a plurality of tubular fluid passageways. These passageways, unlike the tubular sleeve of the previous embodiment, are smaller in diameter than the inflatable balloon and are mounted directly onto its exterior surface. Each passageway is oriented in a substantially longitudinal direction and thus establishes a distal end and a proximal end for the passageway. The distal end of each passageway is sealed to create an infusion duct, and the proximal end of each passageway extends proximally from the balloon to establish a port for fluid access into the fluid duct.

Similar to the previous embodiment having a tubular sleeve, each tubular fluid passageway has at least one injector mounted directly onto its external surface and in fluid communication with the infusion duct. The injectors are located on the surface of the passageway such that upon inflation of the balloon, the injectors travel outwardly in a radial direction. As the balloon continues to expand, each passageway is urged against the arterial wall such that the injectors penetrate into the arterial wall.

The process of injecting a medicament using the embodiment having a tubular fluid passageway is similar to the process using the embodiment with a tubular sleeve. More specifically, the inflatable balloon is positioned along a guide wire in an artery and inflated such that the injectors penetrate the walls of the artery. However, instead of injecting fluid into the infusion chamber created by the tubular sleeve, fluid is injected into the infusion duct created by the tubular fluid passageway. As fluid is pumped into the infusion duct, it is likewise pumped out through the injectors and infused into the arterial wall. Unlike the embodiment with the tubular sleeve, however, each tubular fluid passageway has its own port. Thus, it is possible to administer a variety of medicaments simultaneously, or to administer a particular medicament through one or more selected passageways.

BRIEF DESCRIPTION OF THE DRAWINGS

The novel features of this invention, as well as the invention itself, both as to its structure and its operation will be best understood from the accompanying drawings, taken in conjunction with the accompanying description, in which similar reference characters refer to similar parts, and in which.

DESCRIPTION OF THE PREFERRED EMBODIMENTS

Figure 1:
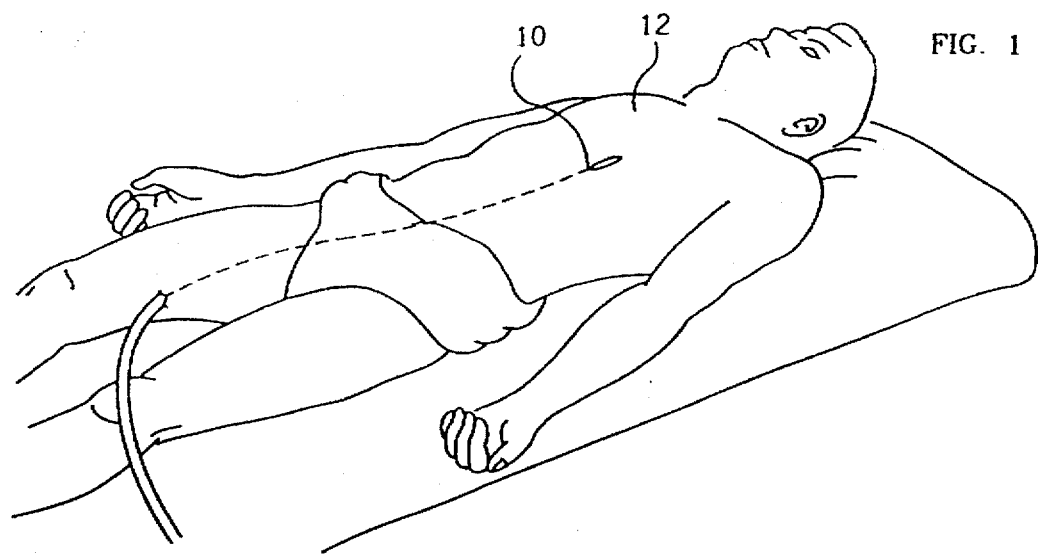
FIG. 1 is a perspective view of a patient with the catheter of the present invention positioned in an artery of the patient for operation of the device.

Referring initially to FIG. 1, a device for injecting fluid medication into the wall of a vessel in accordance with the present invention is shown and generally designated 10. More specifically, the device 10 is shown positioned in the artery of a patient 12. As will be appreciated by the skilled artisan, the device 10 is shown schematically positioned in the patient 12, and it is to be understood that use of the device 10 is not confined to only upper body arteries and vessels but, instead, can be used in arteries and vessels throughout the patient 12.

Figure 2:
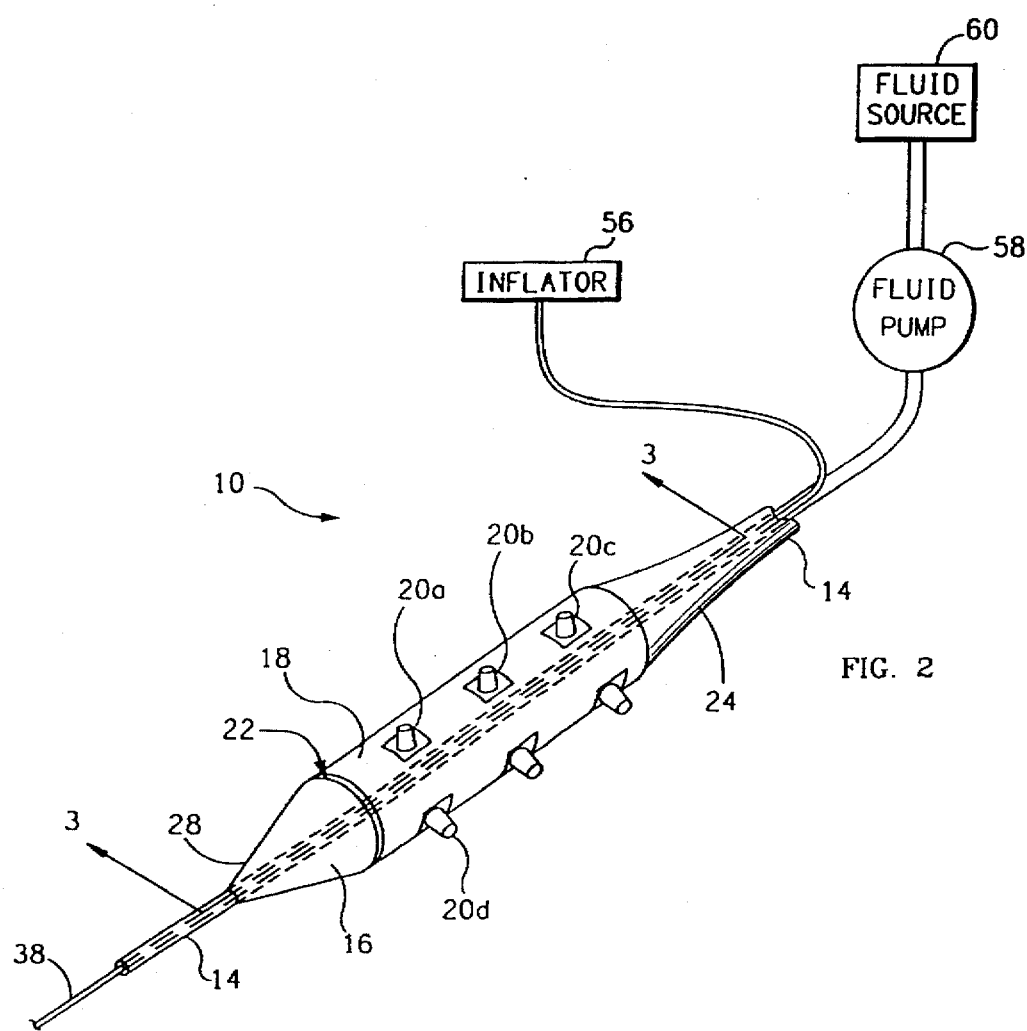
FIG. 2 is a perspective view of the device of the present invention.

FIG. 2 clearly shows that the components of device 10 include a multi-lumen catheter 14 which has an inflatable balloon 16 mounted thereon. Further, FIG. 2 indicates that a tubular sleeve 18 surrounds a substantial portion of the inflatable balloon 16, and that a plurality of injectors 20 are mounted onto the sleeve 18. Of these, the injectors 20a–20b are only exemplary. For purposes of the present invention, balloon 16 is preferably made of polyethylene terephthalate (PET). Additionally, the sleeve 18 can also be made of polyethylene terephthalate (PET).

Figure 3:
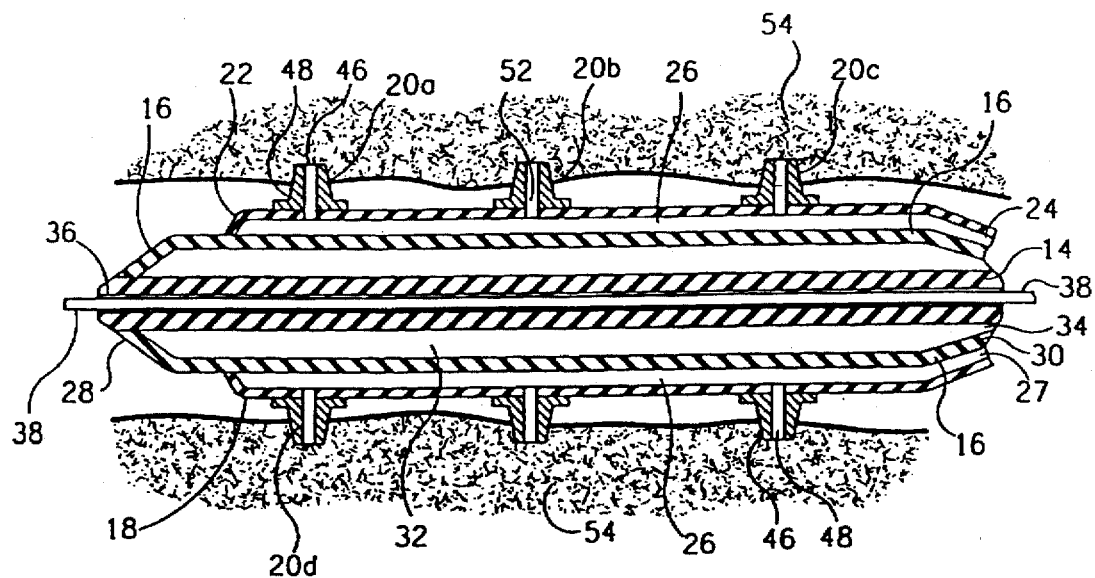
FIG. 3 is a cross-sectional view of the device of the present invention as seen along the line 3—3 in FIG. 2 and positioned in an artery of a patient for infusion of fluid medications into the arterial wall.

A more complete appreciation of the structural cooperation between balloon 16, sleeve 18 and the injectors 20 is provided by FIG. 3 wherein it will be seen that the distal end 22 of sleeve 18 is attached directly to the surface of balloon 16. FIG. 3 also shows that the tubular sleeve 18 substantially surrounds the balloon 16 and that the proximal end 24 of sleeve 18 extends proximally from and beyond the balloon 16 over catheter 14. With this structural relationship, an infusion chamber 26 is formed between the balloon 16 and the sleeve 18. Additionally, as best seen in FIG. 3, a fluid port 27 is formed between the sleeve 18 and catheter 14 through which fluid medication can be injected into the infusion chamber 26.

FIG. 3 further shows that the distal end 28 of balloon 16 is affixed to the catheter 14, and that the proximal end of the balloon 16 closes onto the catheter 14 to create an inflation chamber 32 in the interior of the balloon 16. A port 34 is shown which provides fluid access into the inflation chamber 32. For purposes of the present invention, the port 34 can be connected in fluid communication with a lumen (not shown) of the catheter 14. FIG. 3 also shows that catheter 14 is formed with a lumen 36 which is dimensioned to receive a guidewire 38 therethrough.

Figure 4A:
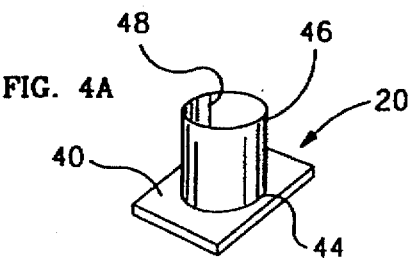
FIG. 4A is a perspective view of an embodiment for a single port injector of the present invention.

Turning now to FIG. 4A, an injector 20 is shown to include a base plate 40 and a hollow protrusion 42 which projects therefrom. Further, it is seen that the end 44 of body 42 is affixed to or integral with the base plate 40. Preferably, the injector 20 is made of nickel and the protrusion 42 is formed by punching out the base plate 40. In any event, a cutting edge 46 is formed around the end of body 42 that is opposite from the end 44 on plate 40 and the resultant structure establishes a fluid channel 48 which extends through the injector 20. As shown, the injector 20 has a substantially cylindrical shaped protrusion 42.

Figure 4B:
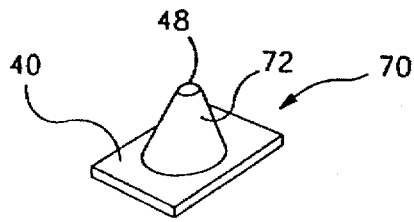
FIG. 4B is a perspective view of another embodiment for a single port injector of the present invention.

In FIG. 4B, another embodiment for an injector of the present invention is shown and designated 70. Rather than having a cylindrical shaped protrusion 42 like the injector 20, however, the injector 70 has a substantially conical shaped protrusion 72. Like injector 20, the injector 70 is preferably made of nickel and is formed to have a fluid channel 48 which extends through the injector 70.

Figure 5A:
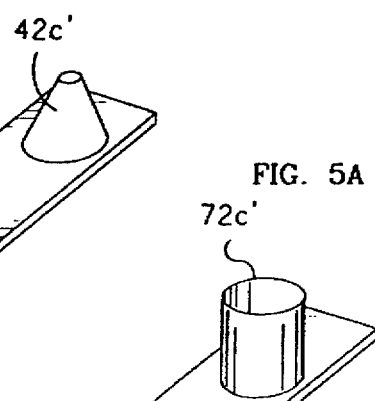
FIG. 5A is a perspective view of an embodiment of a multi-port injector of the present invention.
Figure 5B:
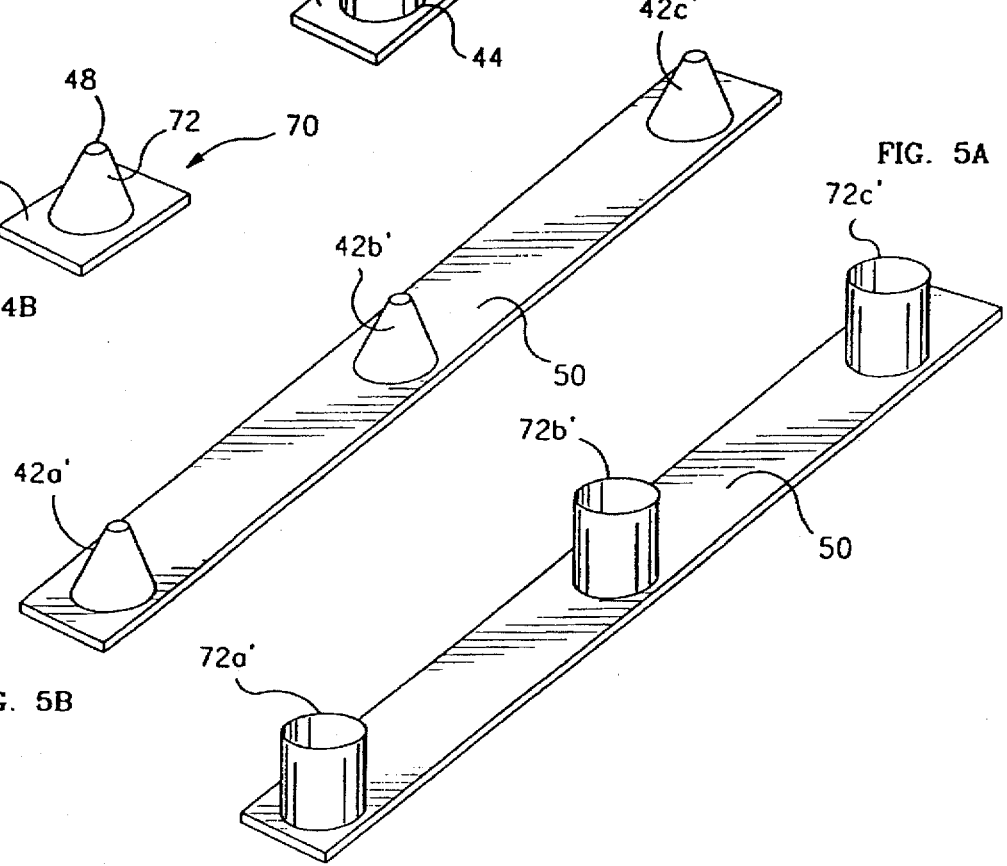
FIG. 5B is a perspective view of another embodiment of a multi-port injector of the present invention.

For a multi-port injector version of the present invention, a plurality of protrusions 42 can be formed from the same base plate. FIG. 5A shows such an embodiment. Specifically, FIG. 5A shows an elongated base plate 50 from which the protrusions 42a', 42b' and 42c' have been formed. In all important respects, the protrusions 42' shown in FIG. 5A are structurally the same as the protrusion 42 discussed above with reference to FIG. 4A. The only difference being that they are collectively mounted on the same base plate 50. Similarly, FIG. 5B shows a multi-port injector wherein the protrusion 72a', 72b' and 72c' have been formed from a base 50. In all important respects, the protrusions 72' shown in FIG. 5B are structurally the same as the protrusion 72 discussed above with reference to FIG. 4B. Again, the only difference being that they are collectively mounted on the same base plate 50.

For purposes of the present invention, the injectors 20 are mounted onto the sleeve 18 so that the channel 48 of each respective injector 20 is aligned with a hole 52 in the sleeve 18. This is done to establish fluid communication between the particular injector 20 and the infusion chamber 26. As a practical matter, it may be preferable in the construction of the device 10 to first mount the injector 20, 70 onto sleeve 18, which can be done in any manner well known in the pertinent art, such as by bonding, and then pierce the sleeve 18 through the channel 48.

In the operation of the present invention the guidewire 38 is first positioned in the vessel to establish a mechanical path for the device 10 to the site, as shown in FIG. 3, where fluid medications are to be infused into a vessel wall 54. Once the balloon 16 of device 10 is properly positioned, an inflator 56 is activated to inflate the balloon 16. As shown in FIG. 2, inflator 56 is connected to the proximal (extracorporeal) end of the device 10. Referring back to FIG. 3, it will be appreciated that, as balloon 16 is inflated, the expanding balloon 16 urges against the tubular sleeve 18 and causes the sleeve 18 to likewise expand. Consequently, the injectors 20, 70 which are mounted on the surface of sleeve 18 move radially from the catheter 14 and are embedded into the vessel wall 54.

With the injectors 20, 70 embedded into the vessel wall 54, the fluid pump 58 shown in FIG. 2 is activated to pump fluid from the fluid source 60 into the infusion chamber 26 through the port 34. Importantly, this pumping action also causes any fluid medication which has already been pumped into the infusion chamber 26 to be expelled through the channels 48 of injectors 20, 70 and into the tissue of vessel wall 54.

After the fluid medication from fluid source 60 has been infused into the vessel wall 54, the balloon 16 can be deflated by reversing the inflator 56. This action will cause the balloon 16 to collapse and to thereby withdraw the injectors 20, 70 from the vessel wall 54. The entire device 10 can then be withdrawn from the patient 12 over the guidewire 38.

Figure 6:
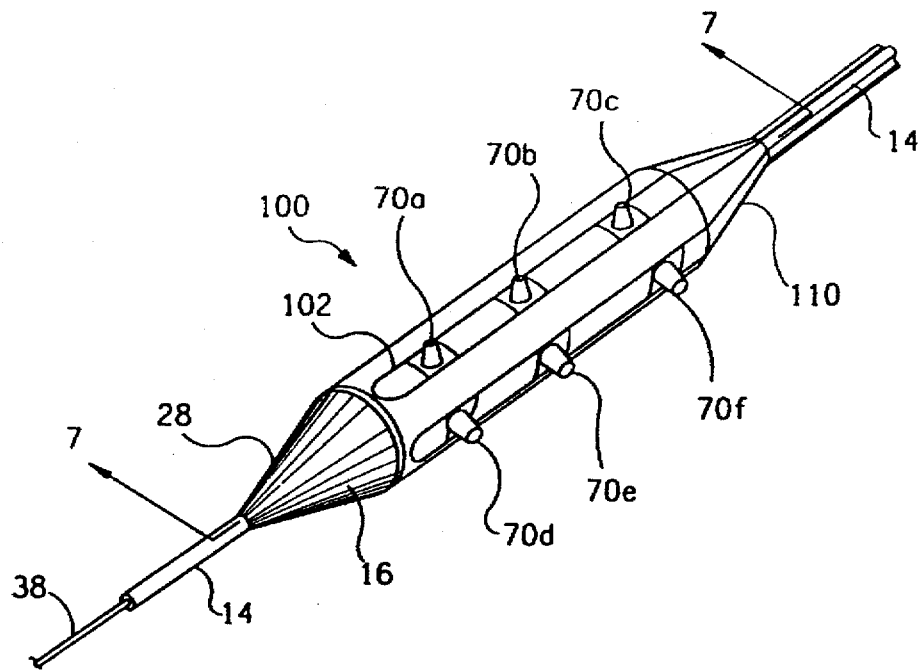
FIG. 6 is a perspective view of another embodiment of the present invention.

In FIG. 6, another preferred embodiment of the present invention is shown. The perspective view in FIG. 6 shows the basic components of device 100, namely, a multi-lumen catheter 14, an inflatable balloon 16 formed to accommodate guide wire 38, and a plurality of tubular fluid passageways 102 mounted on the external surface of balloon 16. Each tubular fluid passageway 102 has a smaller diameter than balloon 16 and is positioned to be substantially parallel with the longitudinal axis of balloon 16.

FIG. 6 further shows that mounted on the surface of each tubular fluid passageway 102 is a plurality of injectors 70. Those injectors 70 are positioned on the outside surface of tubular fluid passageway 102 such that when balloon 16 is inflated, injectors 70 move outwardly in a radial direction. Note, however, the showing of injector 70 is for illustration purposes only and it should be appreciated that any injector or combination of injectors 20/70 discussed in association with the previous embodiments may be used.

Figure 7:
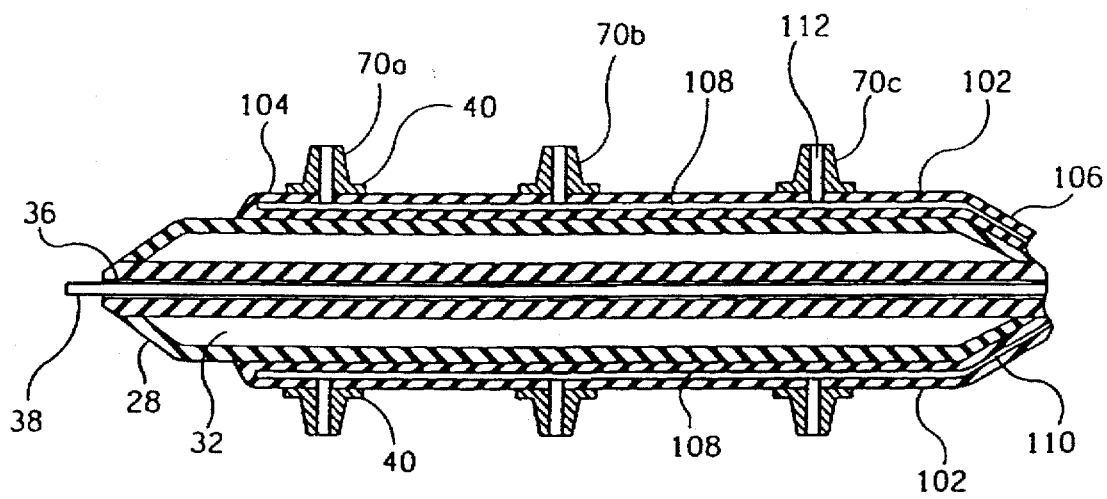
FIG. 7 is a cross-sectional view of the device of the present invention as seen along line 7—7 in FIG. 6.

Referring now to FIG. 7, the cross-sectional view of device 100 shows the tubular fluid passageway 102 in more detail. More specifically, distal end 104 of tubular fluid passageway 102 is sealed to create an infusion duct 108. At proximal end 106 of the tubular fluid passageway 102, port 110 provides fluid access between infusion duct 108 and catheter 14 (not shown). Referring back to FIG. 2, it is appreciated that the proximal (extracorporeal) end of device 100 establishes fluid communication between fluid pump 58 and infusion duct 108. Returning to FIG. 7, injectors 70 are shown mounted on the external surface of tubular fluid passageway 102. As FIG. 7 further shows in detail, base 40 of injector 70 is mounted on tubular fluid passageway 102 over a corresponding hole 112. From this view, it can be appreciated that any number of tubular fluid passageways 102 could be mounted on the external surface of balloon 16. It is further appreciated that any number of injectors 70 could be mounted on a single tubular fluid passageway 102.

Despite the structural differences between the preferred embodiments as discussed above, all of the preferred embodiments operate in much the same manner. More specifically, referring back to FIG. 3, following the positioning of balloon 16 in a vessel, balloon 16 is inflated. As the balloon 16 expands, injectors 70 on tubular fluid passageway 102 are embedded into the vessel wall 54, precisely as detailed above in connection with the previous embodiments. There is, however, a distinction between the embodiments with respect to the connection and activation of fluid pump 58. More precisely, because it is possible to have a plurality of tubular fluid passageways 102, it is likewise possible to either maintain fluid communication with, or fluid isolation between, each tubular fluid passageway 102. For example, fluid communication between tubular fluid passageways 102 can be established by fluidly connecting ports 110 together within catheter 14 such that port 110 of each tubular fluid passageway 102 is supplied fluid from the same fluid pump 58. Alternatively, fluid isolation may be maintained between each tubular fluid passageway 102 by providing each port 110 with a corresponding lumen in catheter 14 establishing its own fluid connection to a corresponding fluid pump 58. Consequently, it is possible to inject a variety of medicaments simultaneously by using a plurality of fluid pumps 58.

While the particular device for injecting medication into the wall of a vessel as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

I claim:

1. A device for injecting fluid medication into a wall of a vessel which comprises:

an inflatable balloon having an outer surface;

means for carrying said fluid medication, said carrying means comprising a plurality of tubular fluid passageways being mounted on said outer surface of said balloon;

means for penetrating the vessel wall, said penetrating means being mounted on said carrying means for fluid communication therewith, said penetrating means including at least one injector;

means for inflating said balloon to urge said penetrating means against the vessel wall to penetrate the vessel wall; and means for infusing said fluid medication in said carrying means through said penetrating means and into the vessel wall.

2. A device as recited in claim 1 wherein said injector comprises:

a base; and a hollow protrusion having a first end and a second end, said protrusion projecting from said base to establish a fluid channel through said base and through said protrusion, said first end of said protrusion being affixed to said base and said second end formed with a cutting edge.

3. A device as recited in claim 1 wherein said penetrating means comprises a plurality of said injectors.

4. A device as recited in claim 1 wherein said injector is substantially conical shaped.

5. A device as recited in claim 1 further comprising a plurality of said penetrating means, each said penetrating means being mounted on a respective said tubular fluid passageway.

6. A device as recited in claim 1 wherein said balloon is made of polyethylene terephthalate (PET).

7. A device as recited in claim 1 further comprising a catheter formed with a lumen, said inflatable balloon being mounted on said catheter with said lumen in fluid communication therewith.

8. A device for injecting fluid medication into a wall of a vessel which comprises:

an inflatable balloon;

at least one tubular fluid passageway mounted on an outer surface of said balloon;

at least one injector mounted on an outer surface of said tubular fluid passageway in fluid communication therewith, said tubular fluid passageway being positioned between the injector and the balloon;

means for inflating said balloon to embed said injector into the vessel wall; and means connectable with said tubular fluid passageway for injecting said medication through said passageway and through said injector into the vessel wall.

9. A device as recited in claim 8 wherein said injector comprises:

a base; and a hollow protrusion having a first end and a second end, said protrusion projecting from said base to establish a fluid channel through said base and through said body, said first end of said protrusion being affixed to said base and said second end formed with a cutting edge.

10. A device as recited in claim 9 further comprising a plurality of said protrusions projecting from said base.

11. A device as recited in claim 10 further comprising a plurality of injectors.

12. A device as recited in claim 9 wherein said protrusion is substantially cylindrical shaped.

13. A device as recited in claim 9 wherein said protrusion is substantially conical shaped.

14. A device as recited in claim 8 which further comprises:

a guidewire;

a catheter formed with a plurality of lumens, one of said lumens being dimensioned to receive said guidewire therethrough for guiding and positioning said balloon in said vessel; wherein said inflatable balloon is mounted on said catheter.

15. A device as recited in claim 14 wherein one of said lumens of said catheter establishes fluid communication between said balloon and said inflating means.

16. A device as recited in claim 8 wherein said inflatable balloon is made of polyethylene terephthalate (PET).

17. A method for injecting medication into a wall of a vessel using a device which includes an inflatable balloon, a tubular fluid passageway mounted on an outer surface of the balloon, at least one injector mounted on an outer surface of said tubular fluid passageway, and said injector being in fluid communication with said tubular fluid passageway, said method comprising the steps of:

positioning said balloon in the vessel;

inflating said balloon to embed said injector into the vessel wall; and selectively injecting medication through said fluid passageway and through said injector into the vessel wall.

\* \* \* \* \*